(12) United States Patent
Triva

(10) Patent No.: US 9,892,508 B2
(45) Date of Patent: Feb. 13, 2018

(54) APPARATUS AND METHOD FOR TREATMENT OF DIAGNOSTIC INFORMATION RELATING TO SAMPLES OF MICROBIOLOGICAL MATERIAL

(71) Applicant: Copan Italia S.P.A., Brescia (IT)

(72) Inventor: Daniele Triva, Brescia (IT)

(73) Assignee: Copan Italia S.p.A., Brescia (IT)

( * ) Notice: Subject to any disclaimer, the term of this patent is extended or adjusted under 35 U.S.C. 154(b) by 0 days.

(21) Appl. No.: 15/109,017

(22) PCT Filed: Dec. 18, 2014

(86) PCT No.: PCT/IB2014/067059
§ 371 (c)(1),
(2) Date: Jun. 29, 2016

(87) PCT Pub. No.: WO2015/101886
PCT Pub. Date: Jul. 9, 2015

(65) Prior Publication Data
US 2016/0328844 A1 Nov. 10, 2016

(30) Foreign Application Priority Data

Jan. 3, 2014 (IT) .............................. MI2014A0004

(51) Int. Cl.
*G06K 9/00* (2006.01)
*G06T 7/00* (2017.01)
(Continued)

(52) U.S. Cl.
CPC ............ *G06T 7/0012* (2013.01); *C12M 41/36* (2013.01); *C12M 41/48* (2013.01); *G01N 1/30* (2013.01);
(Continued)

(58) Field of Classification Search
None
See application file for complete search history.

(56) References Cited

U.S. PATENT DOCUMENTS

| 6,271,022 B1 | 8/2001 | Bochner |
| 2007/0172100 A1 | 7/2007 | Lefebvre |

(Continued)

FOREIGN PATENT DOCUMENTS

WO WO2013004239 A1 1/2013

OTHER PUBLICATIONS

PCT International Search Report and Written Opinion of the International Searching Authority, PCT/IB2014/067059, Mar. 23, 2015, 10 pages.

*Primary Examiner* — Hadi Akhavannik
(74) *Attorney, Agent, or Firm* — Fish & Richardson P.C.

(57) ABSTRACT

An apparatus including a processor; a viewing device operatively connected to the processor; a memory storing a software program that when executed on the processor causes the processor to perform the following operations: defining a user interface on the viewing device, retrieving and visualizing, in the user interface, a datum, or a plurality of data, relative to a same examination site; for retrieving a first image of a first support, of a first type, for microbiological culture, relative to a first microbiological sample coming from the examination site and enabling selective viewing of the first image in the user interface; retrieving a second image of a second support of a second and different type, for microbiological samples, relative to a second microbiological sample coming from the examination site and enabling selective viewing of the second image, to enable the user to make a combined use and evaluation, of the data and of the images.

17 Claims, 5 Drawing Sheets

(51) Int. Cl.
     *C12M 1/34*    (2006.01)
     *C12M 1/36*    (2006.01)
     *G01N 1/31*    (2006.01)
     *G06F 19/00*   (2018.01)
     *G01N 1/30*    (2006.01)
     *G06F 3/048*   (2013.01)
     *G01N 35/00*   (2006.01)

(52) U.S. Cl.
     CPC ............... *G01N 1/31* (2013.01); *G06F 3/048* (2013.01); *G06F 19/321* (2013.01); *G06F 19/366* (2013.01); *G01N 2035/0091* (2013.01); *G01N 2035/00891* (2013.01)

(56) References Cited

U.S. PATENT DOCUMENTS

| | | |
|---|---|---|
| 2009/0137030 A1 | 5/2009 | Wada |
| 2009/0325280 A1 | 12/2009 | Osawa et al. |
| 2010/0082365 A1* | 4/2010 | Noordvyk .............. G06Q 50/22 705/2 |
| 2010/0208960 A1 | 8/2010 | Kiyota |
| 2012/0231517 A1 | 9/2012 | Saez et al. |
| 2013/0165745 A1 | 6/2013 | Wong et al. |

* cited by examiner

APPARATUS AND METHOD FOR TREATMENT OF DIAGNOSTIC INFORMATION RELATING TO SAMPLES OF MICROBIOLOGICAL MATERIAL

CROSS-REFERENCE TO RELATED APPLICATIONS

This application is a U.S. National Phase Application under 35 U.S.C. § 371 and claims the benefit of priority to International Application No. PCT/IB2014/067059, filed on Dec. 18, 2014, which claims the benefit of priority to Italian Application No. MI2014A000004, filed on Jan. 3, 2014, the contents of which are hereby incorporated by reference.

BACKGROUND

The concepts herein relate to an apparatus and a method for treatment of diagnostic information relating to samples of microbiological material. The concepts herein in particular are applicable as a support for carrying out diagnoses in the health, clinical and environmental fields, in all cases in which samples of microbiological materials are to be analysed, and in particular bacteriological material.

As is known, in bacteriological laboratories testing is carried out which, in combination with other evidence obtained from further tests which can be carried out in other laboratories too, combine to convince a doctor of the presence of any infective agent afflicting a patient or which is in a different examination site such as a surface of an environment to be analysed; the final aim of the diagnosis is to lead to prescription, where required, of an adequate therapy, especially of an antibiotic nature, with the aim of neutralizing the pathogen agent identified by the analyses carried out. The microbiologist and the laboratory team, in practice, starting from one or more samples collected from a same examination site, carry out a series of tests, in general following the laboratory guidelines, which often originate from guidelines set down by the Health Ministry or the corporations defining the norms and standards of Good Laboratory Practice.

It is also known that a microbiologist's work method requires an "investigative" approach, characterised by a non-linear process during the course of which outcomes of a series of examinations are obtained in times that can be variable from test to test, the outcomes providing various evidence; and all the preceding is done in a diachronic timescale: for one or more samples collected from a same investigative site various methods made the results available over a timescale that can go from a few minutes to a few days. In particular bacterial cultures can be long in incubation before enabling conclusions to be drawn in relation to the presence or not of bacterial strains in the collected sample. The microbiologist therefore has an iterative approach, as it is often necessary to "re-read" the elements already evaluated previously in the light of new elements to be considered, and vice versa. At present the main method used in bacteriology is the bacterial culture, carried out on media that enable growth, contained in Petri dishes or capsules, following a period of incubation, of bacteria which might afflict a patient and which are present in a biological sample originating from the patient him or herself, such as for example urine, swabs (carried out in one or more anatomical sites), faeces, CSF liquid, respiratory material, etc.

The sample can come from a patient, an animal, or a surface, in cases of applications respectively in the veterinary sector or the environmental sector.

As well as bacterial culture, other methods are known and used in the bacteriological sector, one of the most important of which is Gram-staining, generally carried out on suitable slides, which together with the microscope viewing also provides further evidence on the nature of the pathogen. Other tests used are biochemical in nature and provide further information on the type of pathogen and its belonging to determined classes or families of micro-organisms. In recent years sometimes molecular biology methods are also used, based on DNA and RNA analyses, with the aim of identifying with certainty the presence of a given pathogen, though the cost and specificity of these methods mean that they are used in support of the ones previously described, which are still the most widely-used, as they are less specific and less expensive and complex to perform.

The above-described processes for microbiological analyses are therefore long, complex and difficult to manage, due to the heterogeneity of the tests to be conducted, the iterativity required in the analysis of the single results, and the absence of automated systems for carrying out the laboratory testing and the analysis of the results, which complicate the process of obtaining the correct diagnosis, starting from the interpretation of the single examinations carried out.

Further drawbacks of the known methods are the inefficiency and the lack of unity of the overall process, and the risk of errors in passing information, also due to the lack of a correct consideration of all the information which must contribute to the correct determination of the diagnosis, which are not all contemporaneously accessible to a same subject. Further, the existing systems do not enable sufficient traceability of the whole process carried out and the historical aspect relating to the analyses performed, the devices used and the subjects involved, thus missing a source of information that might be very important in some specific contexts.

The culture dishes themselves are a perishable entity since after some days of incubation the flora normally present in each sample tends to overgrow and "cover" the colonies of the pathogen agent for which identification is sought.

The majority of the work processes performed in the bacteriological laboratory are usually done manually, and only some are done semi-automatically. Recently automatic culture plate-seeding systems have appeared on the market, which have introduced the concept of automation in bacteriology with a consequent standardization of the processes and a greater traceability with respect to manual operations. Digital recording systems of the images of the culture dishes before and after specific incubation periods have also been introduced, together with automated systems of movement of the dishes themselves by conveyor belt. Also known are LIS (Laboratory Information Systems), in which the essential information relating to each patient are collected, such as personal details, which are generally associated to the further data deriving from outcomes of analyses carried out or medical evidence. These systems too, however, enable only marginally obviating those drawbacks mentioned herein above, since these systems are able to transmit only strings of data and not actual information in real-life form, such as for example images.

In certain instances, the concepts herein obviate one or more of the problems encountered in the prior art.

In certain instances, the concepts herein enable eliminating or at least significantly reducing risk of human error in identifying samples to be analysed, in carrying out analytical procedures and/or in determining results thereof.

In certain instances, the concepts herein provide an apparatus and a method for treatment of diagnostic information relating to samples of microbiological material which enable significantly increasing the reliability and the quality of the diagnostic process, and therefore also the safety of the patients.

In certain instances, the concepts herein provide an apparatus and a method for treatment of diagnostic information relating to samples of microbiological material which enable a more rapid, accurate and traced decision on the part of the laboratory doctor concerning the diagnosis.

In certain instances, the concepts herein provide an apparatus and a method for treatment of diagnostic information relating to samples of microbiological material which exhibit a high degree of reliability.

In certain instances, the concepts herein provide an apparatus and a method for treatment of diagnostic information relating to samples of microbiological material which are very flexible and adaptable to various operative requirements.

In certain instances, the concepts herein provide an apparatus and a method for treatment of diagnostic information relating to samples of microbiological material which enable simplification and acceleration of treatment and retrieving processes of the data relating the sample analysis.

In certain instances, the concepts herein provide an apparatus and a method for treatment of diagnostic information relating to samples of microbiological material which provide a high traceability of the historical data relating to the analyses carried out and the devices and subjects involved, so as to enable further studies and statistics to be made on the results themselves.

In certain instances, the concepts herein provide an apparatus and a method for treatment of diagnostic information relating to samples of microbiological material which are simple to realise and which involve sufficiently low costs.

These aims and others besides, which will emerge more fully during the course of the following description, are substantially attained by an apparatus and a method for treatment of diagnostic information relating to samples of microbiological material, according to what is set down in one or more of the accompanying claims, taken alone or in combination with one another, or in any combination with one or more of the further aspects described in the following.

Each of the aspects described in the following can further be taken alone or in any combination with the other described aspects, and further also in combination with any one of the claims of the application or with any combination of the claims.

In certain instances, the concepts herein relate to an apparatus for treatment of diagnostic information relating to samples of microbiological material in which a first software program is configured so as to retrieve, analyse and visualize the data and relative images of the first and second supports relatively to a plurality of patients.

In certain instances, the concepts herein further relate to an apparatus for treatment of diagnostic information relating to samples of microbiological material in which a first software program is configured so as to enable entering comments, symbols and/or graphic signs together with the images, and/or memorising the position of the comments, symbols and/or signs with respect to the images, in order to enable signalling and tracing indications on which the bio-active agents (for example isolated bacterial colonies grown on a culture dish) on which to carry out further tests.

In certain instances, the concepts herein further relates to a method for treatment of diagnostic information relating to samples of microbiological material in which a first image and/or a second image are retrieved from at least a first memory and/or directly from at least an image-acquiring device.

In certain instances, the concepts herein further relate to a method for treatment of diagnostic information relating to samples of microbiological material, wherein a first user interface comprises a plurality of displays or visualization of interface images or screen pages alternatingly representable on the viewing device and reciprocally connected and available directly or indirectly, and the method comprises steps of visualizing the first image, or the first plurality of images, and the second image, or the second plurality of images, in a same interface screen page, or in interface screen pages visualized alternatingly and in succession on the viewing device, and reciprocally mutually connected and available directly or indirectly.

In certain instances, the concepts herein further relate to a method for treatment of diagnostic information relating to samples of microbiological material in which the first biological sample and the second biological sample correspond to one another and originate from a same original sample taken from the first examination site.

In certain instances, the concepts herein further relate to a method for treatment of diagnostic information relating to samples of biological material comprising a step of further viewing in the user interface further metadata associated to the first image, or to the first plurality of images of the first support and/or associated to the second image or second plurality of images of the second support.

In certain instances, the concepts herein further relate to a method for treating diagnostic information relating to samples of micro-biological material further comprising steps of entering and storing further diagnostic data deriving from a combined use and evaluation of the first image, or of the first plurality of images, of the first support, and/or of the second image, or the second plurality of images, of the second support.

In certain instances, the concepts herein further relate to a method for treating diagnostic information relating to samples of micro-biological material further comprising steps of carrying out the analysis of the first image with the aim of evaluating at least the entity and type of the bioactivity of the sample by evaluation of the detected bacteriological growth, by analysis by an operator or by an automatic image interpreting system.

In a further aspect, the concepts hereinfurther relate to a method for treating diagnostic information relating to samples of micro-biological material further comprising steps of retrieving data, from a data system or laboratory information system, and processing and visualizing the data and the relative images of the first and second supports relative to a plurality of patients.

In certain instances, the concepts herein further relate to a method for treating diagnostic information relating to samples of micro-biological material further comprising a step of exchanging data, comprising at least data relating to the first examination site and/or the images relating to samples of micro-biological material, and/or diagnostic data deriving from the combined analysis of the images, between an apparatus for treatment of diagnostic information relating to samples of microbiological material and a laboratory information system.

DESCRIPTION OF THE DRAWINGS

A detailed description is now provided by way of non-limiting example of one or more preferred embodiments of the concepts herein, in which.

DETAILED DESCRIPTION

Figure 1:
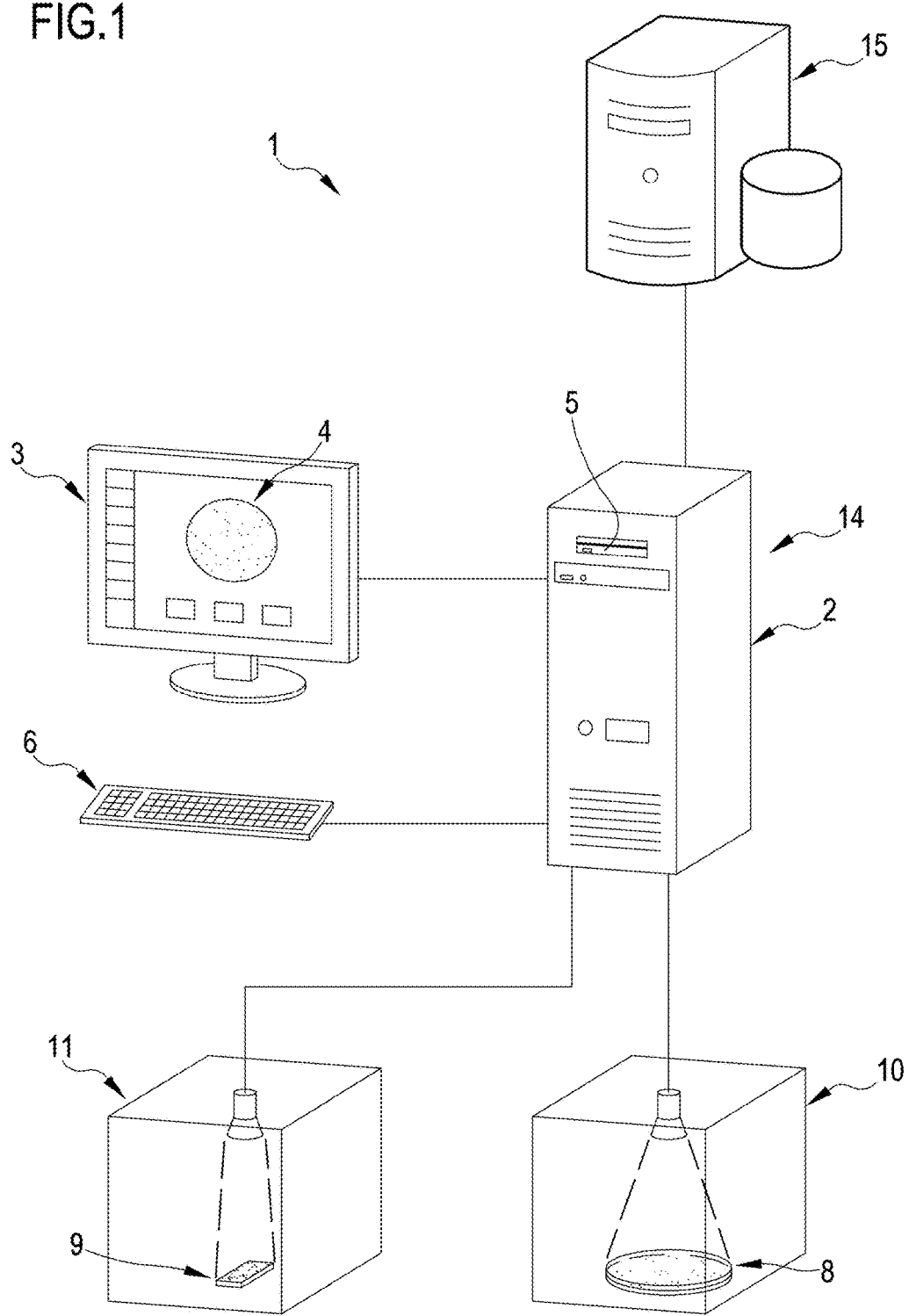
FIG. 1 is a schematic view of an apparatus for treatment of diagnostic information relating to samples of microbiological material according to a first embodiment.
Figure 2:
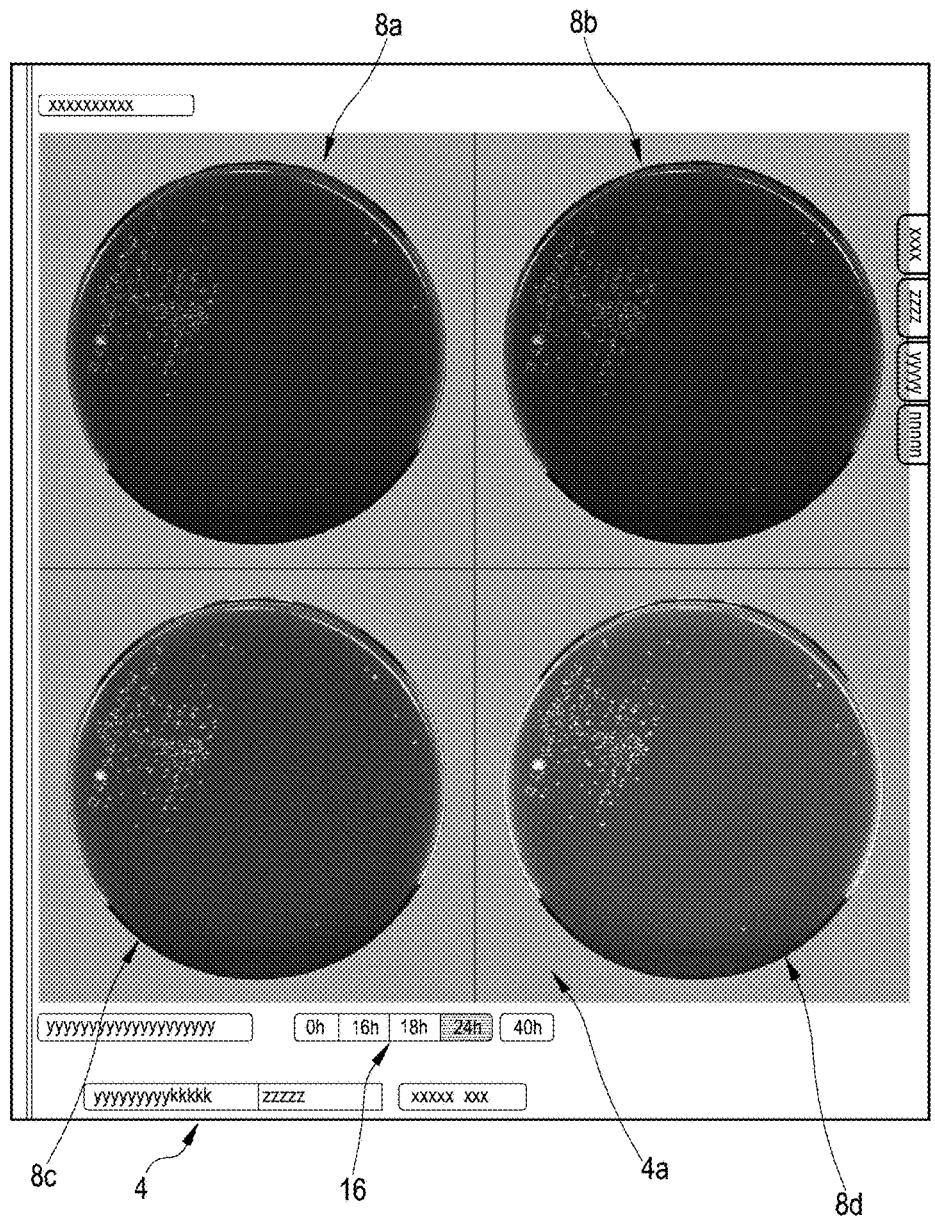
FIG. 2 is a first example screen page display of a first user interface produced on a viewing device by an embodiment of the software program of the apparatus of FIG. 1.
Figure 3:
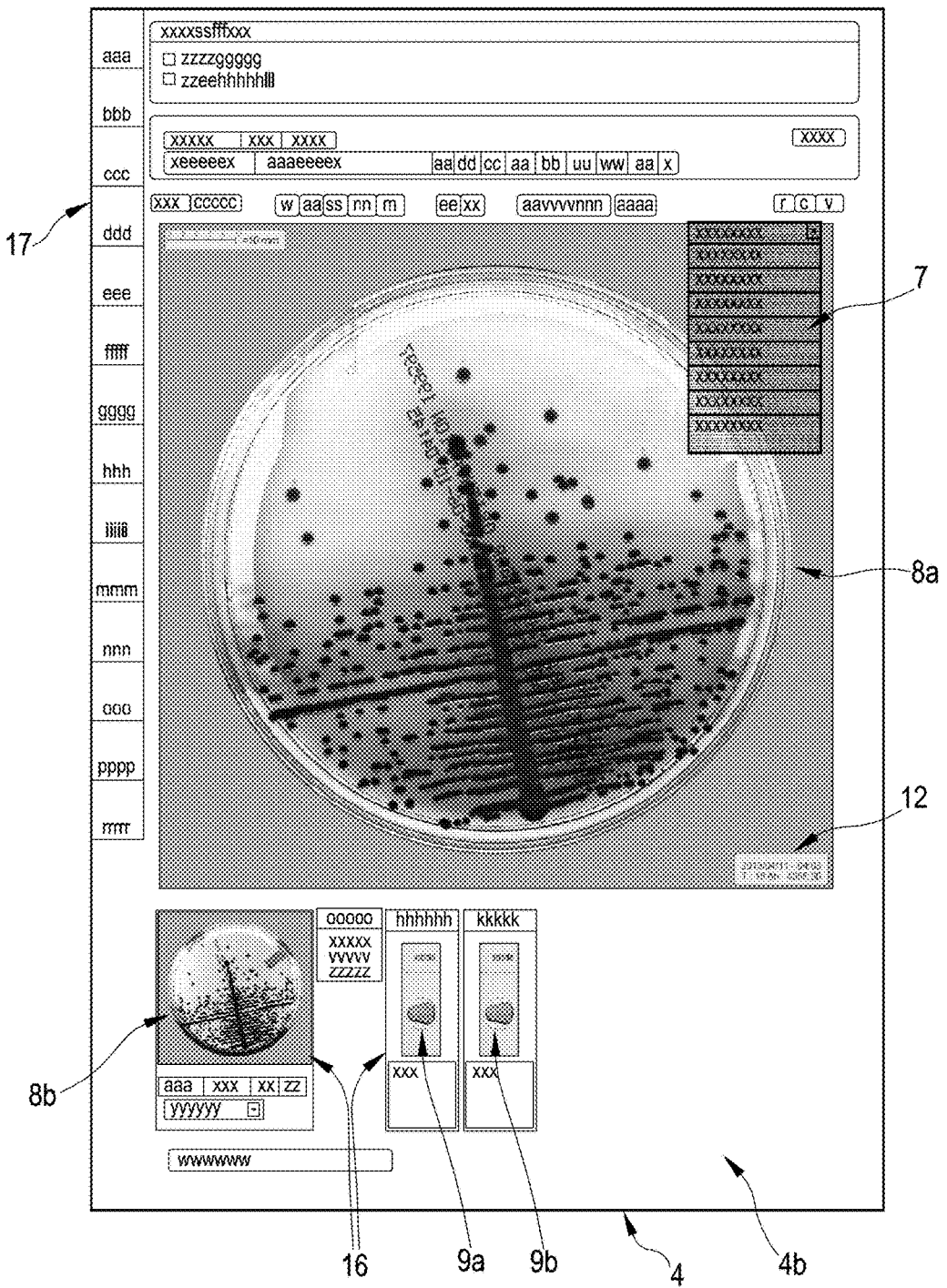
FIG. 3 is a second example screen page display of the first user interface of FIG. 2.
Figure 4:
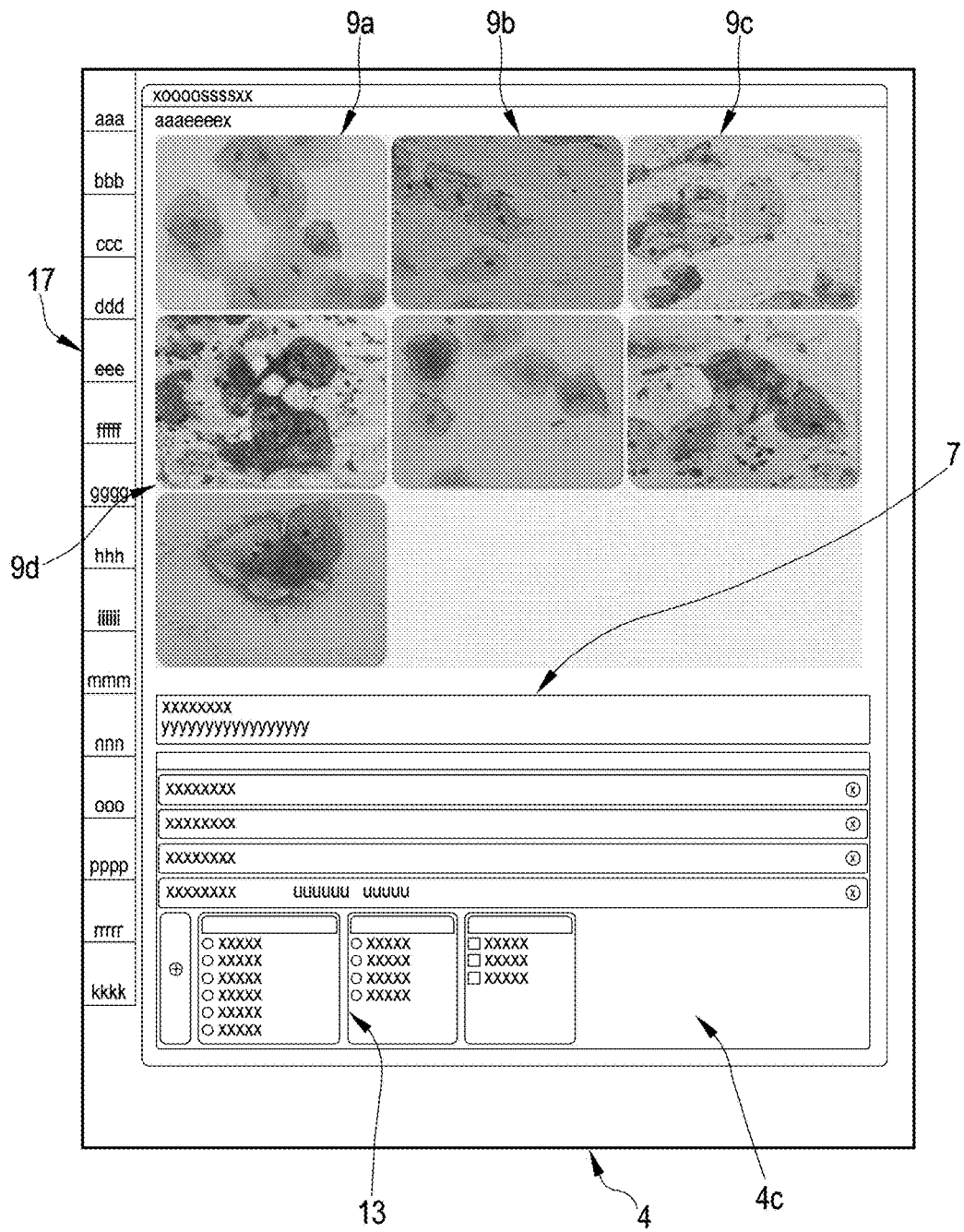
FIG. 4 is a third example screen page display of the first user interface of FIG. 2.

There now follows a description of an apparatus 1 for treatment of diagnostic information relating to samples of microbiological material, according to some embodiments of the concepts herein.

The apparatus 1 comprises at least a first processor 2 and a first viewing device 3, for example a display, operatively connected to the first processor 2.

The apparatus can further comprise a second processor and other processors besides, operatively directly or indirectly connected to the first processor 2 such as to carry out additional functions or part of the functions performed by the first processor 2.

The apparatus 1 further comprises at least a first software program operating on the first processor 2 and configured for defining at least a first user interface 4 on the first viewing device 3. The first software program can be memorized on a local memory 5, associated to the processor, or on an external memory or in a remote location. The first processor 2, the first viewing device 3, as well as the first user interface 4 can also be integrated in a single device, such as for example a tablet or smartphone. In the present text the term "memory" comprises any type of technological system for storing and making accessible data in a digital format, such as for example hard disks, flash memories, rams, roms and so on, locally or remotely available (for example using cloud technology). In the present description the term "software" is taken to comprise both an autonomous program stored and operating locally on the processor, and a web-based program comprising the remote software program accessible via a telematic web or the internet by a browser operating on the processor.

The apparatus 1 preferably comprises a data entry device 6 usable by a user, such as a keyboard, touch-screen, mouse, bar code reader, or another device. The first user interface 4 provides data and image-viewing functions, and further enables entry of data by an operator or user.

The software program can further comprise a data entry function relative to an examination site, an operator or a user by receiving an identifying datum coming from a reading device operatively connected to the apparatus 1 directly or indirectly, such as for example a bar code reader or another reading device suitable for the purpose. In the present text, the term "image" is taken to mean an image in digital format obtained by an appropriate high-defining photographic or television camera, possibly associated to an optical or electronic microscope, as well as by other known systems of image-acquisition, for example by scanning. The image acquisition can also be done by progressive reading and subsequent assembly of partial portions of the support, for example by progressive reading of lines (for example using a linear tv camera) or areas of the support. The first user interface 4 can comprise a plurality of interface screen pages 4a, 4b, 4c representable on the viewing device 3 alternatively and/or contextually. The screen pages are reciprocally connected to one another and can be available one following another, directly, thus by a direct link between two screen pages, or indirectly, i.e. via intermediate screen pages.

The first software program is further configured at least to retrieve and visualize, in the first user interface 4, at least a first datum 7, or a first plurality of data 7, relative to a first examination site. In the present description, the term "examination site" is taken to mean a collecting site in a patient, for example a patient's orifice or another surface at which a biological sample is taken, or a different collecting site with respect to which an analysis is to be performed, and therefore for example also a surface to be analysed in a room or environment.

In the present description, the expression "information relative to an examination site" are taken to mean data of various nature such as for example a patient's personal data, identifying data of a surface to be analysed, identifying data of an examination site, data relating to a bar code, results in the form of text or in numerical form relating to diagnostic examinations carried out, textual data supplied by doctors or laboratory experts, protocols used and the like. In the present description the term "information" does not comprise images.

The first software is further configured such as to retrieve at least a first image 8a of a first support 8, of a first type, for a microbiological culture, in particular a Petri dish provided with Agar medium for bacterial cultures, relative to a first microbiological sample originating from the first examination site and for enabling selective viewing at least of the first image 8a in the first user interface 4.

The first software is further configured such as to retrieve at least a second image 9a of a second support 9 of a second and different type, for microbiological samples, in particular a slide for Gram-staining of micro-organisms and/or a slide for morphological analysis of micro-organisms, relative to a second microbiological sample originating from the first examination site and for enabling selective viewing at least of the second image 9a in the first user interface 4.

The possibility of retrieving and viewing the images 8a of the first support 8 and the images 9a of the second support 9 in a single context enables the user or the specialized operator to carry out a combined analysis of the data relating to the first examination site and of the images relating to the first and/or the second support 9. The combined analysis can be carried out in particular by a simultaneous viewing of the data and images, or by a viewing thereof later on but quite close in terms of time, sufficiently to enable the operator or user to consider all the information that can be drawn from the data and images with the aim of formulating her or his diagnosis.

In this way the operator can at any time reprocess the information already obtained previously in the light of the more recent information received, not being limited to the reading only of a report written on the basis of the previously-analysed images, but with the possibility of viewing the original images (in a digitized form) at the same time or in rapid succession, thus enabling a complete traceability of all the work previously carried out, a significant level of verification, and a reliability and quality in the definition of the diagnosis that is impossible with the traditional systems and approaches.

The first software program is further configured such as to retrieve the first image 8a and/or the second image 9a from at least a first memory 5 operatively connected to the processor. Alternatively the first software program can be configured so as to retrieve the first image 8a and/or the second image 9a directly from at least a first and/or a second device 10, 11 for acquiring images connected to the processor, directly or indirectly.

The first biological sample and the second biological sample can be different though coming from a same examination site, for example a site belonging to a patients, but preferably correspond to one another and originate from a same original sample taken. The first software program can further be configured for retrieving and viewing, selectively or contextually, in the first user interface 4, a first plurality of images 8a, 8b, 8c, 8d etc., of the first support 8 corresponding at least to a corresponding plurality of various time instants correlated to different incubation periods of the first microbiological sample on the first support 9 or Petri dish.

The first software program can further be configured to retrieve and visualise, selectively or contextually, in the first user interface 4, a second plurality of images 9a, 9b, 9c, 9d etc., of the second support 9 corresponding to a corresponding plurality of different time instants or different levels of enlargement, thus at different levels of imaging zoom and images taken by immersion of the lens in oil, of the second sample arranged on the second support 9.

The first software program can further be configured for enabling visualizing at least selectively and alternatively, in the first user interface 4, the first image 8a or the first plurality of images 8a, 8b, 8c, and the second image 9a, or the second plurality of images 9a, 9b, 9c. The first software program can be further configured for further enabling simultaneous viewing in the first user interface 4 of the first image 8a, or the first plurality of images 8a, 8b, 8c, of the first support 8 and the second image 9a, or the second plurality of images 9a, 9b, 9c, of the second support 9.

The first software program can further be configured for enabling viewing, in the first user interface 4, of further metadata 12 associated to the first image 8a, or to the first plurality of images 8a, 8b, 8c, of the first support 8 and/or associated to the second image 9a, or to the second plurality of images 9a, 9b, 9c, of the second support 9. The metadata 12 can comprise, for example, data and/or time of taking the photographic image, the incubation time interval of the support at the moment of taking the image, the place the image was taken at, mode of capture of the image, the device that took the image, etc.

The first software program is further configured for enabling the user to enter and store further data, in particular diagnostic data, deriving from a combined use and evaluation of the first image 8a, or of the first plurality of images 8a, 8b, 8c, of the first support 8, and/or of the second image 9a, or the second plurality of images 9a, 9b, 9c, of the second support 9.

For example, the further data 13 can comprise data relating to the examined micro-organisms, such as the morphology thereof (whether they are coccus, diplococcus, bacillus, streptococcus or yeasts), the Gram-test (i.e. whether they are Gram-positive, Gram-negative or Gram-variable), the quantity or numerousness of the micro-organisms, and so on.

The first software program is further configured so as to retrieve, process and visualise the data and relative images of the first and second supports relative to a plurality of patients, for example with the aim of enabling the operator to carry out a mass screening of the samples in order to identify the macroscopically positive cases, those in which growths or presence of pathogens are evidenced, to which to give priority in the successive laboratory processes. The first software program is configured so as to enable visualizing the first image 8a, or the first plurality of images 8a, 8b, 8c and the second image 9a, or the second plurality of images 9a, 9b, 9c in a same interface screen page, or in interface screen pages 4a, 4b, 4c visualized alternatively and successively on the viewing device 3 and reciprocally connected and available directly or indirectly.

The apparatus 1 further comprises a connecting port 14 configured for, and destined to, enabling operating connection of the apparatus 1 with a laboratory information system 15 or a laboratory technology information system and an exchange of data, monodirectional or preferably bidirectional, between the apparatus 1 and the laboratory information system 15. The information exchanged between the systems comprise at least the data relative to the first examination site and/or the images relative to samples of micro-biological material and/or diagnostic data determined by the user and entered in the first user interface 4. In other terms, the first software program can be provided with numerous functionalities able to increase the practicality of use and the effectiveness of the apparatus 1 as a support in the diagnostic process, such as for example:

user access with customised use configurations, protected by password and other security systems of various types;

possibility of connecting or integrated the apparatus 1 with external systems of both informative type, such as for example a laboratory information system 15 (or LIS), and an instrument system such as for example television cameras, videocameras and/or microscopes able to manually or automatically obtain the images of the supports, including by bar code reading systems or other identifying systems of the supports;

possibility of viewing, simultaneously or side-by-side, images of a same support made at different time instants;

possibility of viewing, simultaneously or side-by-side, images of different types of supports able to provide different information relating to a same microbiological or bacteriological sample;

function of larger-scale viewing of details of the images;

possibility of obtaining textual data, for example personal data, or data originating from instrumental examinations of other types, of patients from external systems, such as a laboratory information system 15 and the like;

possibility of viewing metadata 12 associated to the single images and/or entering further metadata 12 associable to the images;

possibility of entering diagnostic information via the user interface, correlated to the results determined by the users on the basis of the functions offered by the apparatus 1 via the user interface;

possibility of storing the diagnostic information on memories in the apparatus 1 or external thereof;

possibility of sending to external systems, i.e. laboratory information systems and the like, images obtained and/or diagnostic information entered via the user interface on the basis of the analysis of the images;

possibility of retrieving data and images from various information systems and grouping them together according to optimal modalities desired by the users;

possibility for the operator to add comments, symbols and graphic signs on the images, including the ability of the system to memorise the exact position of the signs (for example in the form of Cartesian coordinates or polar coordinates or other types), for example with the aim of signalling (and keep trace of) the indication on which the bioactive agents (for example isolated bacterial colonies grown on a culture dish) on which to perform further tests are located;

presence of connecting elements 16, for example video buttons, for recalling the images relating to various types of support and/or different temporal instants and/or different modalities for acquiring the images;

presence of menus 17 of various types which enable provision of further functionalities for navigating among the different screen pages and/or for activating various functionalities of the software programs, for example for returning to a "home" page, for visualising the images, for receiving or sending data or images to the LIS or to another external device, for generating reports, for modifying imports, and so on.

Figure 5:
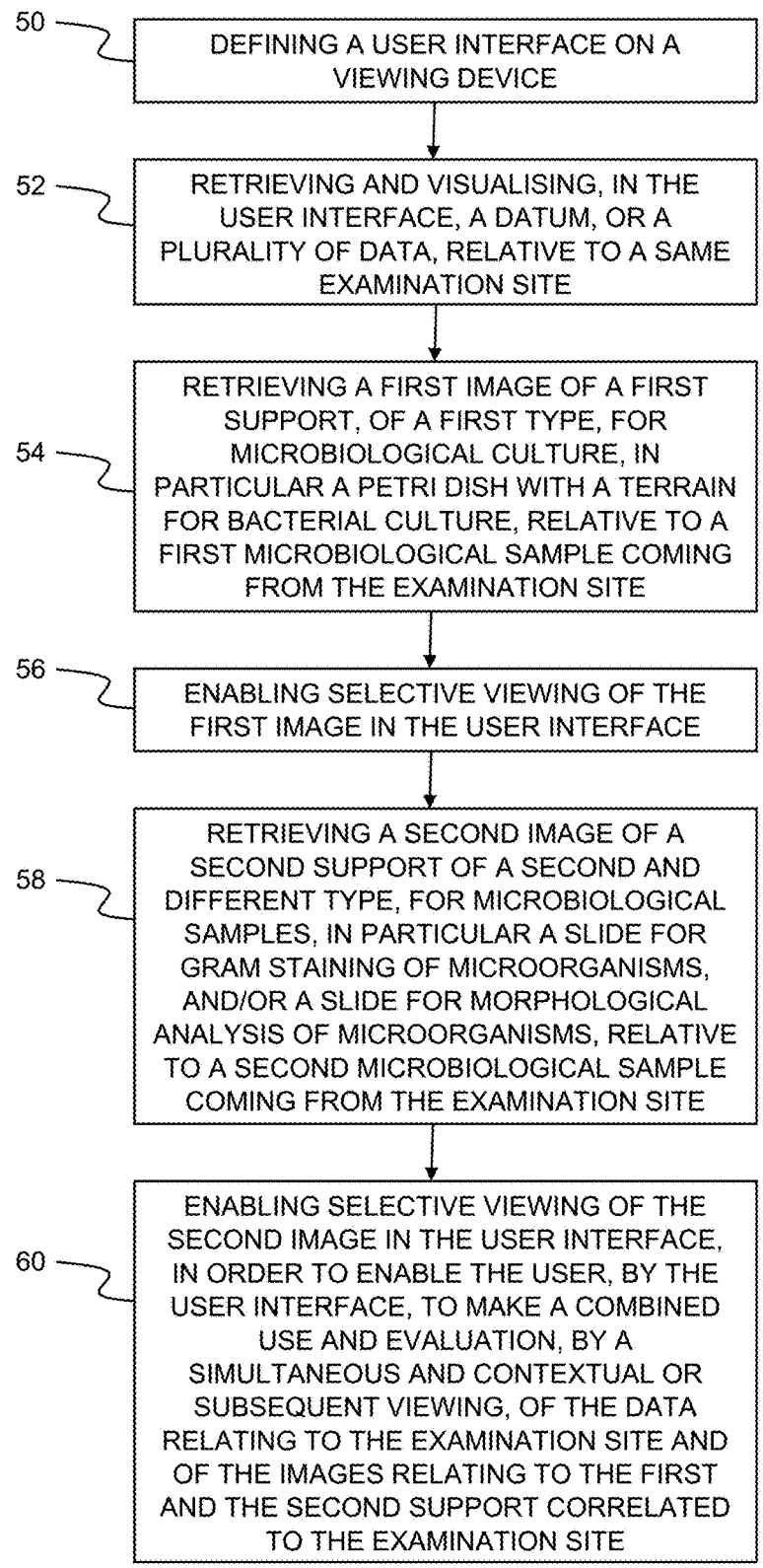
FIG. 5 is a flow diagram depicting an example algorithm of the software program.

The concepts herein further relate to a process for treatment of diagnostic information relating to samples of microbiological material, comprising at least steps of:

defining at least a first user interface 4 on a first viewing device 3 (e.g., operation 50, FIG. 5);

retrieving and visualising, in the first user interface 4, at least a first datum 7, or a first plurality of data 7, relative to a first examination site (e.g., operation 52);

retrieving at least a first image 8a of a first support 8, of a first type, for microbiological culture, in particular a Petri dish with terrain for bacterial cultures, relative to a first microbiological sample coming from the first examination site (e.g., operation 54);

visualising at least the first image 8a in the first user interface 4 (e.g., operation 56);

further retrieving at least a second image 9a of a second support 9 of a second and different type, for microbiological samples, in particular a slide for Gram staining of microorganisms and/or a slide for morphological analysis of microorganisms, relative to a second microbiological sample coming from the first examination site (e.g., operation 58); and visualising at least the second image 9a in the first user interface 4, in order to enable the user to make a combined use and evaluation of the data relating to the first examination site and of the images relating to the first and the second support 9 (e.g., operation 60).

The method can further comprise steps of retrieving and visualising, selectively or contextually, in the first user interface 4, a first plurality of images 8a, 8b, 8c of the first support 8 corresponding at least to a corresponding plurality of different time instants correlated to different incubation periods of the first microbiological sample on the first type of support or Petri dish. The method can further comprise steps of retrieving and visualizing, selectively or contextually, in the first user interface 4, a second plurality of images 9a, 9b, 9c of the second support 9 corresponding to a corresponding plurality of different time instants or different levels of enlargement or to a different mode of image-detecting of the second sample arranged on the second support 9.

The method can further comprise steps of visualizing at least selectively and alternatingly, in the user interface, the first image 8a or the first plurality of images 8a, 8b, 8c, and the second image 9a or the second plurality of images 9a, 9b, 9c. The process can further comprise steps of simultaneously visualizing, in the user interface, the first image 8a, or the first plurality of images 8a, 8b, 8c, of the first support 8 and the second image 9a, or the second plurality of images 9a, 9b, 9c, of the second support 9.

The first image 8a and/or the second image 9a can be retrieved for example from at least a first memory and/or directly from at least a device 10, 11 for acquiring images.

The method can further comprise steps of displaying the first image 8a, or the first plurality of images 8a, 8b, 8c and the second image 9a, or the second plurality of images 9a, 9b, 9c in a same interface screen page, or in interface screen pages 4a, 4b, 4c viewed alternatively or successively on the viewing device 3 and reciprocally connected to one another and available directly or indirectly.

The method can comprise steps of further visualizing, in the user interface, further metadata 12 associated to the first image 8a, or to the first plurality of images 8a, 8b, 8c of the first support 8 and/or associated to the second image 9a, or to the second plurality of images 9a, 9b, 9c of the second support 9.

The method can further comprise steps of inserting and memorising further diagnostic data 13 deriving from a combined analysis of the first image 8a, or the first plurality of images 8a, 8b, 8c of the first support 8 and/or the second image 9a, or the second plurality of images 9a, 9b, 9c of the second support 9.

The method can further comprise steps of retrieving, from a laboratory information system 15, processing and visualizing the data and/or the relative images of the first and second supports relatively to a plurality of patients.

The method can further comprise the steps of exchanging information, comprising at least data relative to the first examination site and/or the images, relative to samples of microbiological material, and/or diagnostic data deriving from the combined fruition and evaluation of the images, between an apparatus 1 for treatment of diagnostic information relative sample of microbiological material and a laboratory information system 15.

The concepts herein enable obtaining one or more of the following advantages.

Primarily, the concepts herein enable obviating the problems encountered in the prior art.

The concepts herein further enable a rapid, accurate and traced decision on the part of the bacteriologist and the laboratory doctor regarding the diagnosis, based not only on other evidence (relative to bacterial growths on culture dish) by indeed having access to the digitized original images of the dishes and supports.

The concepts herein further enable a simplification and acceleration of the treatment methods and a retrieval of the information relative to the analyses of the samples. The concepts herein further enable eliminating or at least significantly reducing the risk of human error in identifying the samples to be analysed, in carrying out the analytic procedures and/or in determining the results thereof.

The concepts herein further offer a high degree of reliability and repeatability of the results, and makes available an apparatus and a method which are extremely flexible and adaptable to various operational needs and various types of analysis.

The concepts herein further enable simplification of the treatment processes of the information relating to the analyses of the analysed samples.

The concepts herein further enable simplifying the treatment processes of the information relative to the analyses of the analysed samples.

The concepts herein further enable complete traceability of the historical information relative to the analyses carried out and the devices and subjects involved, and further enables summings-up, studies and statistics on the results themselves.

The concepts herein further enable significantly increasing the reliability and quality of the diagnostic process, the safety of the analytical processes of the samples, and therefore also the safety of the patients.

Lastly, the concepts herein are simple and convenient to actuate.

The invention claimed is:

1. An apparatus for treatment of diagnostic information relating to samples of microbiological material, in which the apparatus comprises:
 a processor;
 a viewing device operatively connected to the processor; and
 a memory storing a software program that when executed on the processor causes the processor to perform the following operations:
 defining a user interface, for treatment of diagnostic information relating to samples of microbiological material, on the viewing device and retrieving and visualising, in the user interface, a datum, or a plurality of data, relative to a same examination site;
 retrieving a first image of a first support, of a first type, for microbiological culture, where the first support comprises a Petri dish with a terrain for bacterial culture, relative to a first microbiological sample coming from the examination site and enabling selective viewing of the first image in the user interface;
 retrieving a second image of a second support of a second and different type, for microbiological samples, where the second support comprises a slide for Gram staining of microorganisms, and/or a slide for morphological analysis of microorganisms, relative to a second microbiological sample coming from the examination site and enabling selective viewing of the second image in the user interface, in order to enable the user, by the user interface, to make a combined use and evaluation, by a simultaneous and contextual or subsequent viewing, of the data relating to the examination site and of the images relating to the first and the second support correlated to the examination site.

2. The apparatus of claim 1, wherein the software program when executed operating on the processor further causes the processor to retrieve the first image and/or the second image from a first memory operatively connected to the processor.

3. The apparatus of claim 1 wherein the software program when executed operating on the processor further causes the processor to retrieve the first image and/or the second image directly from a first device for acquiring images operatively connected to the processor.

4. The apparatus of claim 1 wherein the first microbiological sample and the second microbiological sample are corresponding to one another and deriving from a same original sample collected from the examination site.

5. The apparatus of claim 1, wherein the software program when executed operating on the processor further causes the processor to retrieve and visualize, selectively or contextually, in the user interface, a first plurality of images of the first support corresponding to a corresponding plurality of different time instants correlated to different incubation periods of the first microbiological sample on the first support.

6. The apparatus of claim 1, wherein the software program when executed operating on the processor further causes the processor to retrieve and visualize, selectively or contextually, in the user interface a second plurality of images of the second support corresponding to a corresponding plurality of different time instants or different levels of enlargement or different modes of image detecting of the second sample arranged on the second support.

7. The apparatus of claim 1, wherein the software program when executed operating on the processor further causes the processor to visualize selectively and alternatively, in the user interface, the first image or first plurality of images, and the second image, or second plurality of images.

8. The apparatus of claim 1 wherein the software program when executed operating on the processor further causes the processor to enable simultaneous viewing in the user interface of the first image, or first plurality of images, of the first support and the second image, or second plurality of images, of the second support.

9. The apparatus of claim 1, wherein the user interface comprises a plurality of interface screen pages representable on the viewing device alternatingly and reciprocally connected and available, directly or indirectly, and wherein the software program when executed operating on the processor further causes the processor to visualize the first image, or first plurality of images, and the second image, or the second plurality of images, in a same interface screen page, or in interface screen pages visualized alternatingly and in succession on the viewing device, and reciprocally mutually connected and available directly or indirectly.

10. The apparatus of claim 1, wherein the software program when executed operating on the processor further causes the processor to enable viewing, in the user interface, of further metadata associated to the first image, or to a first plurality of images, of the first support and/or associated to the second image, or to a second plurality of images, of the second support.

11. The apparatus of claim 1, wherein the software program when executed operating on the processor further causes the processor to enable the user to enter and store further data, in particular diagnostic data, deriving from a combined use and evaluation of the first image, or of first plurality of images, of the first support, and/or of the second image, or second plurality of images, of the second support.

12. The apparatus of claim 1, further comprising a connecting port configured for, and destined to, enabling operating connection of the apparatus with a laboratory information system or a laboratory technology information system and an exchange of data, comprising at least one of the data relating to the examination site, the images relating to samples of microbiological material or diagnostic data determined by the user and entered in the user interface, between the apparatus and the laboratory information system.

13. A process for treatment of diagnostic information relating to samples of microbiological material, comprising steps of:
 defining a user interface, for treatment of diagnostic information relating to samples of microbiological material, on a viewing device;
 retrieving and visualising, in the user interface, a datum, or a plurality of data, relative to an examination site;
 retrieving a first image of a first support, of a first type, for microbiological culture, where the first support comprises a Petri dish with terrain for bacterial cultures, relative to a first microbiological sample coming from the examination site;

visualising the first image in the user interface;

further retrieving a second image of a second support of a second and different type, for microbiological samples, where the second support comprises a slide for Gram staining of microorganisms and/or a slide for morphological analysis of microorganisms, relative to a second microbiological sample coming from the examination site; and visualising the second image in the user interface, in order to enable the user to make a combined use and evaluation, by simultaneous or subsequent viewing, of the data relating to the examination site and of the images relating to the first and the second support related to the examination site.

14. The process of claim 13, comprising steps of retrieving and visualising, selectively or contextually, in the user interface, a first plurality of images of the first support corresponding to a corresponding plurality of different time instants correlated to different incubation periods of the first microbiological sample on the first support.

15. The process of claim 13, comprising steps of retrieving and visualizing, selectively or contextually, in the user interface, a second plurality of images of the second support corresponding to a corresponding plurality of different time instants or different levels of enlargement or to a different mode of image detecting of the second sample arranged on the second support.

16. The process of claim 13, further comprising steps of visualizing selectively and alternatingly, in the user interface, the first image or first plurality of images, and the second image or second plurality of images.

17. The process of claim 13, further comprising steps of simultaneously visualizing, in the user interface, the first image, or first plurality of images, of the first support and the second image, or second plurality of images, of the second support.

* * * * *